United States Patent
Dee et al.

(10) Patent No.: US 7,220,432 B2
(45) Date of Patent: May 22, 2007

(54) VEGETABLE SUBSTITUTE FOR LANOLIN

(75) Inventors: Gary J. Dee, Gulph Mills, PA (US);
Norman Milstein, Cincinnati, OH (US); Barry A. Salka, Fair Lawn, NJ (US); Judy Zhuang, Blue Bell, PA (US); Stefan Bruening, Philadelphia, PA (US)

(73) Assignee: Cognis Corporation, Ambler, PA (US)

( * ) Notice: Subject to any disclaimer, the term of this patent is extended or adjusted under 35 U.S.C. 154(b) by 174 days.

(21) Appl. No.: 10/686,478

(22) Filed: Oct. 15, 2003

(65) Prior Publication Data

US 2004/0161484 A1 Aug. 19, 2004

Related U.S. Application Data

(63) Continuation-in-part of application No. 10/393,149, filed on Mar. 20, 2003.

(60) Provisional application No. 60/373,973, filed on Apr. 19, 2002.

(51) Int. Cl.
*A61K 9/00* (2006.01)
*A61K 7/00* (2006.01)

(52) U.S. Cl. ............... 424/489; 424/401; 424/70.1; 424/78.03; 424/78.05

(58) Field of Classification Search ............... 514/169; 552/500; 424/78.02, 78.03, 78.05, 489, 401, 424/70.1
See application file for complete search history.

(56) References Cited

U.S. PATENT DOCUMENTS 6,316,030 B1 * 11/2001 Kropf et al. ............... 424/489

* cited by examiner

*Primary Examiner*—Sabiha N. Qazi
(74) *Attorney, Agent, or Firm*—John F. Daniels; Daniel S. Ortiz

(57) ABSTRACT

Lanolin-free lanolin substitute compositions comprising:
A) from about 5 to about 95% by weight, of at least one plant sterol fatty acid ester;
B) from about 1 to about 20% by weight, of at least one polyglyceryl di-polyhydroxy fatty acid ester;
C) from about 1 to about 20% by weight, of at least one polyglyceryl di-fatty acid ester;
D) from about 0.25 to about 10% by weight of at least one glyceryl fatty acid ester; and
E) optionally, from about 1 to 80% by weight of an additive containing a mixture of (i) a vegetable oil, (ii) a hydrogenated vegetable oil, and (iii) a non-petroleum derived wax.

14 Claims, No Drawings

VEGETABLE SUBSTITUTE FOR LANOLIN

CROSS REFERENCE TO RELATED APPLICATION

This application is a continuation-in-part of copending application Ser. No. 10/393,149 filed on Mar. 20, 2003, and claims priority of Ser. No. 60/373,973 filed on Apr. 19, 2002.

FIELD OF THE INVENTION

This invention relates to a vegetable substitute for lanolin.

BACKGROUND OF THE INVENTION

Lanolin is a product obtained by the purification of degras. Degras is a crude grease obtained by the solvent treatment of wool.

Lanolin is a yellowish to gray semisolid containing 25 to 30% water in its hydrous form, and a brownish-yellow semisolid in its anhydrous form. Lanolin contains cholesterol esters of higher fatty acids.

Lanolin is used as a component of pharmaceuticals, leather finishing compositions, soaps and detergents, face creams, facial tissues, hair-set compositions, suntan preparations, and the like.

SUMMARY OF THE INVENTION

This invention relates to lanolin substitute compositions derived from vegetable materials, which are lanolin-free. The lanolin substitute compositions of the invention comprise the following components.

A) from about 5 to about 95% by weight, preferably from 15 to 60% by weight, of a plant sterol fatty acid ester, preferably soya sterol fatty acid esters;

B) from about 1 to about 20% by weight, preferably from 5 to 15% by weight, of a polyglyceryl di-polyhydroxy fatty acid ester, preferably di-polyhydroxy stearate;

C) from about 1 to about 20% by weight, preferably from 5 to 15% by weight, of a polyglyceryl di-fatty acid ester, preferably diisostearate;

D) from about 0.25 to about 10% by weight, preferably from 1 to 5% by weight of a glyceryl fatty acid ester, preferably oleate; and E) optionally, from about 1 to about 80% by weight of an additive containing:
 (i) a vegetable oil;
 (ii) a hydrogenated vegetable oil; and
 (iii) a non-petroleum derived wax component.

In addition to the above components, the compositions can also optionally contain other compatible components including one or more of the following components:

F) a microcrystalline wax;

G) a polyethyleneglycol plant sterol, preferably PEG-5 soya sterol; and

H) a petrolatum/mineral oil

DETAILED DESCRIPTION OF THE INVENTION

Other than in the operating examples, or where otherwise indicated, all numbers expressing quantities of ingredients or reaction conditions used herein are to be understood as modified in all instances by the term "about".

When the lanolin substitute compositions of the invention contain one or more of the above named optional components, the optional components can be present in the following quantities:

E) additive—from about 1 to about 80% by weight, preferably from about 15 to 70% by weight, and most preferably from about 35 to 60% by weight;

F) microcrystalline wax—up to about 20% by weight, preferably from about 1 to 20% by weight, and more preferably from about 5 to 15% by weight.

G) polyethyleneglycol plant sterol—up to about 20% by weight, preferably from about 1 to 20% by weight, and more preferably from about 5 to 15% by weight.

H) petrolatum/mineral oil—up to about 60% by weight, preferably from about 1 to 60% by weight, and more preferably from about 20 to 40% by weight.

The percentages of components A) through D) as well as optional components E) through H) can vary according to the performance characteristics desired in the finished product, such as water absorption, iodine value, melting point, and the like.

Component A) can be any plant sterol fatty acid ester in which the fatty acid moiety is derived from a saturated or olefinically unsaturated, straight or branched chain fatty acid containing from 6 to 22 carbon atoms, preferably from 16 to 18 carbon atoms. The preferred sterol is soya sterol, which is a mixture of stigmasterol and sitosterols (dihydrostigmasterols).

Component B) can be any polyglyceryl di-polyhydroxy fatty acid ester in which the fatty acid moieties are independently derived from a polyhydroxy saturated or olefinically unsaturated, straight or branched chain fatty acid containing from 6 to 22 carbon atoms, preferably from 16 to 18 carbon atoms, and most preferably 18 carbon atoms. The polyglyceryl moiety can contain from 2 to 12 glyceryl groups, preferably 2 groups. Each polyhydroxy fatty acid moiety can contain from 2 to 8 hydroxy groups. Preferred compounds are those in which each fatty acid moiety is identical.

Component C) can be any polyglyceryl di-fatty acid ester in which each fatty acid moiety is independently derived from a saturated or unsaturated, straighter branched chain fatty acid containing from 6 to 22 carbon atoms, preferably from 16 to 18 carbon atoms, and most preferably 18 carbon atoms. Preferred compounds are those in which each fatty acid moiety is identical. The polyglyceryl moiety can contain from 2 to 12 glyceryl groups, preferably 3 groups.

Component D) can be any glyceryl fatty acid mono-, di-, or tri-ester in which the fatty acid moiety is independently derived from a saturated or olefinically unsaturated, straight or branched chain fatty acid containing from 6 to 22 carbon atoms, preferably from 16 to 18 carbon atoms, and is most preferably derived from oleic acid.

Component E) is an additive containing a mixture of (i) from about 0.5 to about 95% by weight, preferably from about 10 to about 90% by weight, and most preferably from about 70 to about 90% by weight of a vegetable oil, (ii) from about 0.1 to about 50% by weight, preferably from about 5 to about 20% by weight, and most preferably from about 5 to about 15% by weight of a hydrogenated vegetable oil, and (iii) from about 0.01 to about 30% by weight, preferably from about 0.1 to about 15% by weight, and most preferably from about 1 to about 10% by weight of a non-petroleum derived wax, all weights being based on the total weight of the composition.

Component F) is microcrystalline wax which is a wax that is usually composed of branched-chain paraffins, characterized by a crystalline structure much smaller than that of normal wax.

Component G) is a polyethyleneglycol plant sterol containing from 2 to 10, and preferably 5 ethyleneglycol groups. The plant sterol is preferably soya sterol.

Component H) is a mixture of from 50 to 100% by weight of petrolatum, a petroleum jelly, and from 0 to 50% by weight of white mineral oil, which is a mixture of liquid hydrocarbons.

The compositions of the invention can be prepared by mixing the components together at a temperature of from 50 to 100° C., preferably from 70 to 75° C.

It has also been discovered that compositions comprising polyol esters and petrolatum can be employed as lanolin substitutes. Such compositions contain from 5 to 20% by weight of polyol ester, preferably from 8 to 10% based on the weight of petrolatum.

The above lanolin substitutes can consist of just the above components, or can contain one or more additional components that are compatible therewith, such as one or more of components A) through H) set forth above, in quantities that do not change the lanolin-like characteristics of the components.

The polyol esters can include one or more of sorbitan fatty acid esters and alkyl glycoside esters.

The sorbitan fatty acid esters are esters of $C_4$–$C_{22}$, preferably $C_6$–$C_{18}$, alkyl or alkenyl fatty acids, which can be straight or branched chain. Examples include, but are not limited to, sorbitan monolaurate, sorbitan monooleate, sorbitan monostearate, sorbitan monopalmitate, and sorbitan tristearate.

The alkyl glycoside esters are $C_2$–$C_{20}$ alkyl or alkenyl carboxylic acid esters of a reducing saccharide or polysaccharide in which the saccharide contain 5 or 6 carbon atoms, preferably esters of glucoside or a polyglucoside, which also contain an alkyl or alkenyl radical containing from 1 to 20 carbon atoms.

The alkyl glycoside esters have the formula I:

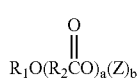

$$R_1O(R_2CO)_a(Z)_b \quad \text{(I)}$$

wherein $R_1$ is a $C_1$–$C_{20}$ alkyl or alkenyl group, $R_2$ is a $C_3$–$C_2$, alkyl or alkenyl group, preferably derived from vegetable fatty acids, a is an integer of from 1 to 4, preferably from 2 to 4, Z is a saccharide residue containing 5 or 6 carbon atoms, preferably 6 carbon atoms, and b is a number of from 1 to 6.

The preferred compound of formula I is methyl glucoside dioleate.

The invention will be illustrated but not limited by the following examples.

EXAMPLES

The following components listed in Table 1 were mixed together with stirring at a temperature of 70–75° C. until homogeneous:

TABLE 1

| Ingredient | INCI | Ex. 1 | Ex. 2 | Ex. 3 | Ex. 4 |
|---|---|---|---|---|---|
| soya sterol sunflowerate | | 77.5 | 60.0 | 38.5 | 17.5 |
| CEGESOFT ® VP[(1)] | veg. oil + hydrogenated veg. oil + candelilla wax | | 17.5 | 39.0 | 60.0 |
| DEHYMULS ® PGPH[(2)] | polyglyceryl-2-dipolyhydroxystearate | 10.0 | 10.0 | 10.0 | 10.0 |
| LAMEFORM ® TGI[(3)] | polyglyceryl-3-diisostearate | 10.0 | 10.0 | 10.0 | 10.0 |
| MONOMULS ® 90-018[(4)] | glyceryl oleate | 2.5 | 2.5 | 2.5 | 2.5 |

[(1)–(4)]Sold by Cognis Corp., Care Chemicals, Ambler, PA

The following components listed in Table 2 were mixed together with stirring at a temperature of 70–75° C. until homogeneous:

TABLE 2

| Ingredient | INCI | Ex. 5 | Ex. 6 | Ex. 7 |
|---|---|---|---|---|
| Microcrystalline Wax Multiwax W-835 | microcrystalline wax | | | 7.0 |
| Petrolatum Blend HE | petrolatum and white mineral oil | 30.0 | 40.0 | 50.0 |
| soya sterol sunflowerate | | 30 | 22 | 10 |
| CEGESOFT ® VP[(1)] | veg. oil + hydrogenated veg. oil + candelilla wax | 9 | 25 | 20 |
| DEHYMULS ® PGPH[(2)] | polyglyceryl-2-dipolyhydroxystearate | 15 | 6 | 6 |
| LAMEFORM ® TGI[(3)] | polyglyceryl-3-diisostearate | 15 | 6 | 6 |
| MONOMULS ® 90-018[(4)] | glyceryl oleate | 1 | 1 | 1 |

What is claimed is:

1. A lanolin-free lanolin substitute composition comprising the following components:
   A) from 5 to about 95% by weight of at least one plant sterol fatty acid ester;
   B) from about 1 to about 20% by weight of at least one polyglyceryl di-polyhydroxy fatty acid ester;
   C) from about 1 to about 20% by weight of at least one polyglyceryl di-fatty acid ester;
   D) from about 0.25 to about 10% by weight of at least one glyceryl fatty acid ester; and
   E) optionally, from about 1 to 80% by weight of an additive containing a mixture of (i) a vegetable oil, (ii) a hydrogenated vegetable oil, and (iii) a non-petroleum derived wax.

2. The composition of claim 1 wherein component A) is present in from about 15 to about 60% by weight, components B) and C) are present in from about 5 to about 15% by weight, component D) is present in from about 1 to about 5% by weight, and component E) is present in an amount of from about 35 to 65% by weight, all weights being based on the weight of the composition.

3. The composition of claim 1 wherein component A) is soya sterol fatty acid ester, component B) is polyglyceryl-2 di-polyhydroxystearate, component C) is polyglyceryl-3 diisostearate, and component D) is glyceryl oleate.

4. The composition of claim 2 wherein component A) is soya sterol fatty acid ester, component B)is polyglyceryl-2 di-polyhydroxystearate, component C) is polyglyceryl-3 diisostearate, and component D) is glyceryl oleate.

5. A lanolin-free lanolin substitute composition of claim 1 comprising the following components:
 A) about 40% by weight of soya sterol $C_{18}$ saturated fatty acid ester;
 B) about 10% by weight of polyglyceryl-2 polyhydroxystearate;
 C) about 10% by weight of polyglyceryl-3 diisostearate;
 D) about 2.5% by weight of glyceryl oleate; and
 E) about 37.5% of the additive.

6. The composition of claim 1 wherein the composition also contains at least one of the following components:
 F) microcrystalline wax;
 G) a polyethyleneglycol plant sterol; and
 H) petrolatum/mineral oil.

7. The composition of claim 6 wherein component F) is present in from 1 to about 20% by weight, component G) is present in from 1 to about 20% by weight; and component H) is present in from 1 to 60% by weight, all weights being based on the total weight of the composition.

8. The composition of claim 6 wherein at least component F) is present and wherein component G) is polyethyleneglycol soya sterol.

9. In the formulation of a pharmaceutical, cosmetic composition, soap, detergent, or leather finishing composition in which lanolin is used as a component thereof, the improvement wherein the composition of claim 1 is used in place of lanolin.

10. In the formulation of a pharmaceutical, cosmetic, soap, detergent, or leather finishing composition in which lanolin is used as a component thereof, the improvement wherein the composition of claim 5 is used in place of lanolin.

11. In the formulation of a pharmaceutical, cosmetic, soap, detergent, or leather finishing composition in which lanolin is used as a component thereof, the improvement wherein the composition of claim 6 is used in place of lanolin.

12. In the formulation of a pharmaceutical, cosmetic composition, soap, detergent, or leather finishing composition in which lanolin is used as a component thereof, the improvement wherein the composition of claim 9 is used in place of lanolin.

13. The composition of claim 1 wherein B) comprises polyglyceryl di-polyhydroxystearate.

14. The composition of claim 13 wherein A) comprises soya sterol fatty acid ester.

* * * * *